US006905833B2

(12) United States Patent
Nguyen

(10) Patent No.: US 6,905,833 B2
(45) Date of Patent: Jun. 14, 2005

(54) METHOD OF DIAGNOSING BREAST CANCER USING NIPPLE FLUID

(75) Inventor: Mai H. Nguyen, Thousand Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 340 days.

(21) Appl. No.: 09/901,339

(22) Filed: Jul. 9, 2001

(65) Prior Publication Data

US 2002/0086341 A1 Jul. 4, 2002

Related U.S. Application Data

(60) Provisional application No. 60/217,372, filed on Jul. 11, 2000.

(51) Int. Cl.[7] .............................................. G01N 33/53
(52) U.S. Cl. ...................................... 435/7.23; 436/501
(58) Field of Search ................................ 435/711, 7.23; 436/501; 514/9; 530/387.7, 387.9, 388.24

(56) References Cited

U.S. PATENT DOCUMENTS 5,187,062 A    2/1993  Sato et al.

OTHER PUBLICATIONS

Sauter et al., Br J Cancer. Dec. 1999;81(7):1222–7.*
Products for Life Sciences Research (200–2001 Sigma Catalog, p. 979 only).*
Nguyen, 1997, Investigational New Drugs, 15:29–37.*
Relf, et al., 1997, Cancer Research, 57(5):963–3.*
Li, et al 1994, The Lancet, 344: 82–86.*
Cheales–Siebenaler, et al., 1999, Journal of Human Lactation, 15(1):41–3.*
Cheales–Siebenaler, Noreen J., "Induced Lactation in an Adoptive Mother," Journal of Human Lactation, Mar. 1999, 15(1):41–3. (Exhibit 2).
Foretova, Lenka et al., "Carcinembryonic Antigen in Breast Nipple Aspirate Fluid," Cancer Epidemiology, Biomarkers and Prevention, Mar. 1998, 7:195–8. (Exhibit 3).
Fujimoto, Kiyohide et al., "Increased Serum Levels of Basic Fibrolast Growth Factor in Patients with Renal Cell Carcinoma," Biochemical and Biophysical and Research Communications, Oct. 15, 1991, 180(1):386–92. (Exhibit 4).
Gail, Mitchell H. et al., "Projecting Individualized Probabilities of Developing Breast Cancer for White Females Who Are Being Examined Annually," Journal of the National Cancer Institute, Dec. 20, 1989, 81(24):1879–86. (Exhibit 5).
Gann, Peter et al., "Mitogenic Growth Factors in Breast Fluid Obtained from Healthy Women: Evaluation of Biological and Extraneous Sources of Variability," Cancer Epidemiology, Biomarkers and Prevention, Jun. 1997, 6(6):421–8. (Exhibit 6).

Li, Vincent W. et al., "Microvessel Count and Cerebrospinal Fluid Basic Fibroblast Growth Factor In Chidren With Brain Tumours," Lancet, Jul. 9, 1994, 344:82–6. (Exhibit 7).
Lin, Richard Y. et al., "Diagnostic and Prognostic Role of Basic Fibroblast Growth Factor In Wilms' Tumor Patients," Clinical Cancer Research, Mar. 1995, 1:327–31. (Exhibit 8).
Nguyen, Mai, "Angiogenic Factors as Tumor Markers," Investigational New Drugs, 1997, 15:29–37. (Exhibit 9).
Nguyen, Mai et al., "Elevated Levels of an Angiogenic Peptide, Basic Fibroblast Growth Factor, in the Urine of Patients with a Wide Spectrum of Cancers," Journal of National Cancer Institute, Mar. 2, 1994, 86(5):356–61. (Exhibit 10).
O'Brien, T.S. et al., "Urinary Basic Fibroblast Growth Factor in Patients with Bladder Cancer and Benign Prostatic Hypertrophy," British Journal of Urology, 1995, 76:311–4. (Exhibit 11).
Petrakis, Nicholas L., "Nipple Aspirate Fluid in Epidemiologic Studies of Breast Disease," Epidemiologic Reviews, 1993, 15(1):188–95. (Exhibit 12).
Rose, David P., "Hormones and Growth Factors in Nipple Aspirates from Normal Women and Benign Breast Disease Patients," Cancer Detection and Prevention, 1992, 16(1):43–51. (Exhibit 13).
Sauter, Edward R. et al., "Prostate–Specific Antigen Levels in Nipple Aspirate Fluid Correlate with Breast Cancer Risk," Cancer Epidemiology, Biomarkers and Prevention, Dec. 1996, 5:967–70. (Exhibit 14).
Sluitz, G. et al., "Serum Evaluation of Basic Fibroblast Growth Factor in Cervical Cancer Patients," Cancer Letters, 1995, 94(2):227–31. (Exhibit 15).
Takei, Yoshifumi et al., "Serum Concentrations of Basic Fibroblast Growth Factor in Breast Cancer," Clinical Chemistry, 1994, 40(10):1980–1. (Exhibit 16).
Watanabe, H. et al., (Abstract) "Basic Fibroblast Growth Factor in Human Serum—A Prognostic Test for Breast Cancer," Molecular Biology of the Cell (formerly Cell Regulation) Abstracts, Sep. 1992, 3:234a. (Exhibit 17).
Watanabe, Hiroyuki et al., "A Sensitive Enzyme Immunoassay for Human Basic Fibroblast Growth Factor," Biochemical and Biophysical Research Communications, Feb. 28, 1991, 175(1):229–35. (Exhibit 18).

(Continued)

Primary Examiner—Larry R. Helms
Assistant Examiner—Misook Yu
(74) Attorney, Agent, or Firm—Suzannah K. Sundby; Smith, Gambrell & Russell, LLP

(57) ABSTRACT

Methods and kits for detecting breast cancer or a high risk of breast cancer by measuring bFGF in nipple fluid from subjects compare the levels of bFGF in samples from test subjects with the levels of bFGF in subjects not having breast cancer, where increased levels of bFGF in test subjects indicate the presence of breast cancer, or a high risk of breast cancer, in the test subjects.

8 Claims, No Drawings

OTHER PUBLICATIONS

Wrensch, Margaret et al., "Breast Cancer Risk Associated with Abnormal Cytology in Nipple Aspirates of Breast Fluid and Prior History of Breast Biopsy," *American Journal of Epidemiology*, Apr. 15, 1993, 137(8):829–33. (Exhibit 19).

Wrensch, Margaret R. et al., "Factors Associated with Obtaining Nipple Aspirate Fluid: Analysis of 1428 Women and Literative Review," *Breast Cancer Research and Treatment*, 1990, 15:39–51. (Exhibit 20).

Liu, Yeheng et al., "Breast–Cancer Diagnosis with Nipple Fluid bFGF," *The Lancet*, Aug. 12, 2000, 356(9229):567. (Exhibit 21).

Reilly, Thomas M. et al., "Monoclonal Antibodies Directed Against Basic Fibroblast Growth Factor Which Inhibits Its Biological Activity In Vitro and in Vivo," *Biochemical and Biophysical Research Communications*, Oct. 30, 1989, 164(2):736–43. (Exhibit 22).

* cited by examiner

METHOD OF DIAGNOSING BREAST CANCER USING NIPPLE FLUID

This application is based on a provisional application U.S. Ser. No. 60/217,372, filed Jul. 11, 2000, the contents of which are hereby incorporated by reference, in their entirety into this application.

Throughout this application, various publications are referenced. The disclosures of these publications in their entireties, are hereby incorporated by reference into this application, in order to more fully describe the state of the art, as known to those skilled therein, as of the date of invention, described and claimed herein.

FIELD OF THE INVENTION

The present invention relates to methods for diagnosing the presence of breast cancer, and more particularly to the measurement of basic fibroblast growth factor (bFGF) in nipple fluid, to detect breast cancer in a subject.

BACKGROUND OF THE INVENTION

Breast cancer is the most frequently diagnosed cancer in American women. It is the leading cause of death in young women under 50 years of age, and is the second most common cause of cancer death among American women. The key to increasing survival is early diagnosis. Early detection through screening mammography saves lives. However, mammography misses as much as 20% of the breast cancer in premenopausal women and 10% in older women. Breast biopsies resulting from abnormal mammograms confirm cancer in only 10–20% of the cases.

While intense effort has been invested in refining the resolution and interpretation of mammography, little has been devoted to the search for tumor markers that may assist in detecting minute amounts of breast cancer. Current serum tumor markers for breast cancer are only useful in cases of widespread disease. (Harris J R, Morrow M, Norton L. Malignant tumors of the breast. In: DeVita V T, Hellman S, Rosenberg S A, eds., In Cancer: principles and practice of oncology. Philadelphia: Lippincott-Raven, (1997).

Recently, there has been increased interest in the possible use of angiogenic factors as tumor markers. In the past few decades, researchers have become increasingly interested in the observation that tumor growth and metastasis are accompanied by significant new blood vessel formation, i.e. angiogenesis. Angiogenic factors have been found associated with several solid tumors such as retinoblastomas and osteosarcomas. Studies have shown that angiogenic factors can be significantly elevated in the serum and urine of breast cancer patients. The levels of certain angiogenic factors have been shown to correlate with the disease stage of the tumor. (Nguyen M., *Invest New Drug* (1997)).

Approximately 15 angiogenic peptides have been identified and sequenced, including basic fibroblast growth factor (bFGF). (Folkman J, In The molecular basis of cancer, Mendelsohn et al., (eds), W B Saunders, pp 206–232 (1995)). These angiogenic molecules are either released by the tumor cells themselves, or mobilized from extracellular matrix and/or released by host cells, such as macrophages recruited into the tumor.

bFGF, one of the most potent angiogenic factors, has been reported to be widely distributed among normal and neoplastic tissue (Folman J, sura). bFGF is a member of a family of heparin binding growth factors found in a variety of normal and neoplastic tissues. A method for detecting and measuring bFGF using a sandwich immunoassay method is described in U.S. Pat. No. 5,187,062 to Sato et al. A sensitive assay for the detection of bFGF in bodily fluids was not reported until 1991 (Watanabe et al., *Biochem. Biophys. Res. Comm.* 175:229–235, (1991)), with the first clinical use reported by Fujimoto et al., *Biochem. Biophys. Res. Comm.* 180:386–392 (1991)). bFGF was elevated in serum of patients with renal cell carcinoma, but was not detected in the urine of these patients. Only 6% of 235 patients with breast cancer had detectable bFGF (>39 pg/ml) using the Watanabe bioassay (Watanabe et al., (Abstract) *Molec. Biol. Cell* 3S:234a (1992)). An elevated level of bFGF has been found in the urine of patients with a variety of tumors including kidney, bladder, prostate, testicular, breast, colon, lung, brain, ovarian, sarcoma and lymphoma (Nguyen et al., *J. Natl. Cancer Inst.* 86:356–361 (1994)).

Improvements in the ELISA used for detecting FGF have permitted improved detection of bFGF in urine from subjects with bladder tumors (O'Brien et al., *Br. J. Urol.* 76:311–314 (1995)), Wilms' tumors (Lin et al., *Clin. Cancer Res.* 1:327–331 (1995)) and in serum of patients suffering from cervical cancer (Sliutz et al., *Cancer Lett.* 94:227–231 (1995)). Takei et al. (*Clin. Chem.* 40:1980–1981 (1994)) measured serum bFGF in patients with breast cancer and found significant elevations in all stages of disease.

The level of bFGF (basic fibroblast growth factor) has been shown to correlate with the disease stage of the tumor. (Nguyen M, Watanabe H, Budson A, Richie J, Hayes D, Folkman J, *J Natl Cancer Inst.*, 86: 356–61 (1994)). However, thus far, use of bFGF in urine or serum samples cannot be used as a screening tool, since there is significant overlap in levels of bFGF between normal subjects and cancer patients. (Nguyen et al., *J. Natl. Cancer Inst.*, supra, and Nguyen M., *Invest. New Drug.*, 15: 29–37 (1997)).

bFGF has also been detected in the cerebrospinal fluid (CSF) of patients with brain tumors but not in controls; the level of bFGF correlated with mitogenic activity in CSF in vitro and with density of microvessels in histological sections (Li et al., *Lancet* 344:82–86 (1994)).

Angiogenic factors may be useful as markers of therapeutic efficacy and to assess an individual cancer patient's prognosis. Previously elevated urine bFGF levels have been shown to decrease into the normal range following complete surgical removal of tumors. Patients with progressive disease had increased bFGF levels detected after repeat urine samples. (Nguyen et al., *J. Natl. Cancer Inst.* 86:356–361 (1994)).

Breast cancer arises from the epithelial cells that line the ductal/lobular systems of the milk ducts suggesting that examination of this ductal system or its secretions might reveal signs of early cancer. Breast fluid contains immunoglobulins, proteins, lipids, cholesterol, fatty acids, lactose and hormones including prolactin, growth hormone-like protein, EGF and TGFα, calcitonin and insulin-like growth factor (IGF) (Rose, *Cancer Det. Prev.,* 16:43–51 (1992); and Gann et al., *Cancer Epidemiol., Biomarkers & Prev.*, 6:421–8 (1997)). Breast fluid is typically prevented from escaping from the nipple because the nipple ducts are occluded by constricting bands of smooth muscle, viscous and dried secretions and keratinized epithelium (Petrakis, *Epidemiol. Rev.* 15:188–195 (1993)).

Patients' nipple fluid (nipple aspirate fluid or "NAF") has not been extensively investigated as a possible source for breast cancer diagnostic purposes. Factors associated with the success of obtaining NAF include age, (subjects within the age range of 30 to 50 years), subjects having early onset of menarche, subjects of non-Asian race, and subjects with prior lactation. (Wrensch et al., *Breast Cancer Res. Treatm.* 15:39–51 (1990)).

Prior studies have attempted to detect cancer cells in NAF, but technical difficulties have included a paucity of cancer cells, probably because the cancer obstructs the ducts, and difficulty in distinguishing cancer cells from dyplastic cells. (Wrensch et al., *Am. J. Epidemiol.*, 137:829–33 (1993)). Previous studies with nipple fluid CEA (carcinoembryonic antigen) and PSA (prostate specific antigen) showed significant overlap between the study groups. (Foretova L, Garber J E, Sadowsky N L, Verselis S J, Joseph D M, Andrade A F F, Gudrais P G, Fairclough D, Li F P. Carcinoembryonic antigen in breast nipple aspirate fluid. *Cancer Epidemiol Biomark Prevent*, 7: 195–8 (1998); and Sauter E R, Daly M, Linahan K, Ehya H, Engstrom P F, Bonney G, Ross E A, Yu H, Diamandis E. Prostate-specific antigen levels in nipple aspirate fluid correlate with breast cancer risk. *Cancer Epidemiol Biomark Prevent*, 5: 967–70 (1996)).

There remains a need for improved diagnostic methods for breast cancer that are better able to distinguish between normal subjects and those having breast cancer.

SUMMARY OF THE INVENTION

Accordingly, the present invention provides improved methods for diagnosing breast cancer or a high risk of breast cancer, by measuring bFGF levels in nipple fluid obtained from human subjects. The method employs a bioassay for quantitation of bFGF in nipple fluid using, for example, anti-bFGF antibody, and comparing the levels of bFGF in test subjects with levels in subjects not having cancer, an increase in the level of bFGF in the test sample, as compared to samples form subjects not having cancer, indicating breast cancer, or high risk of breast cancer. The methods include diagnostic kits for measuring bFGF levels in nipple fluid.

DETAILED DESCRIPTION OF THE INVENTION

The present invention is based on the discovery of measurable amounts of bFGF in breast fluid, and provides methods for detecting, quantifying and comparing levels of bFGF in a sample of nipple fluid from a subject. The subject may be a human or an animal.

Concentrations of bFGF are determined in the sample of nipple fluid from a test subject and are compared to concentrations of bFGF present in samples taken from multiple human subjects known to be free of breast cancer ("normals"). In the examples, infra, levels of bFGF were increased in subjects having breast cancer or at high risk of having breast cancer as compared to levels of bFGF in samples taken from the breasts of normal subjects. Values for levels of bFGF from samples from subjects diagnosed with breast cancer, or at risk for breast cancer, did not overlap with levels from normal subjects.

Concentrations of bFGF may also be determined over successive time intervals to determine the progress of breast cancer in a subject, or to determine the efficacy of therapeutic intervention. In addition, the method of the invention can include the detection of other cancer markers, such as other angiogenic factors including, but not limited to, acidic FGF (aFGF), vascular endothelial growth vector (VEGF), epidermal growth factor (EGF), transforming growth factor-alpha and beta (TGF-α and TGF-β), hepatocyte growth factor (HGF), tumor necrosis factor-alpha (TNF-α), interleukin-8 (IL-8), granulocyte colony stimulating factor (G-CSF), E-selectin, angiogenin, platelet-derived endothelial cell growth factor (PD-ECGF), placental growth factor and pleiotrophin, angiogenic inhibitors such as thrombospondin, TIMP, angiostatin, endostatin, platelet factor 4, maspin. In addition, other cancer markers may be detected, including, but not limited to CA125, Tac, soluble IL2 receptor alpha, mCSF, OVX1, CEA, PSA, CA15–3 and CA19.9.

Preferably, levels of bFGF are measured in a subject prior to significant trauma such as surgery or chemotherapy, because of the release of growth factors following such events, and the possibility of duct blockage from scarring, hematomas or seromas. Also, due to the elevation of bFGF in breast milk, sample results may be best in subjects that have ceased lactating for at least 1 year.

It is preferred to obtain sufficient nipple fluid, for example from 10 μl to 1 ml. to promote sampling from all regions of the breast to enhance detection of cancer. In addition, since bFGF is a labile peptide, it is preferred to assay as soon as possible after sampling, and without repeated freezing, and thawing of the sample.

Since nipple fluid is typically not spontaneously discharged, samples are preferably obtained in a manner that optimizes the yield of fluid, yet preserves the comfort of the human subject. For example, a warm compress may be applied to the breast of the subject in an upright (seated) position. To encourage fluid removal, keratin plugs that may be present blocking the ducts in the nipple may be removed, for example using dilute (5 to 15%) salicylic acid. Alternatively, or in addition, drugs such as oxytocin, salagen or prolactin may be given to encourage fluid flow. For example, nasal oxytocin can be used to relax the constricting bands of smooth muscle in the breast to enhance flow of nipple fluid for sampling. Nasal oxytocin has been approved by the FDA since 1982 and has been used safely in lactating as well as in non-lactating women (Cheales-Siebenaler, J. Hum. Lact. 15:41–43 (1999); Renfrew et al., Cochrane Database Syst. Rev. 2:CD000156, (2000)). If necessary, sufficient breast fluid from a subject for assay may be obtained using assistive means such as a ductoscope or microcatheter.

Concentrations of bFGF in nipple fluid may be measured using various known techniques. In the example, infra, an ELISA assay (R & D Systems Inc., Minneapolis, Minn.) using anti-bFGF antibodies is used. However, other assay methods employing reagents that can bind to and/or detect bFGF may be used, including radioimmunoassays or chemiluminescent assays.

A model has been developed for predicting breast cancer risk (Gail et al., J. Natl. Cancer Inst. 81:1879–1886 (1989). A woman's risk factors are translated into an overall risk score by multiplying her relative risks from several categories (age at menarche, number of breast biopsies, family history and age at first live birth). This risk score is then multiplied by an adjusted population risk of breast cancer to determine the individual risk of breast cancer.

The methods of the invention may be performed using pre-packaged diagnostic kits. Such kits include reagents, such as monoclonal antibodies, for assaying bFGF levels in nipple fluid samples, and reagents for detecting the binding of antibodies to bFGF present in the sample, as well as agents such as sucralfate to inhibit degradation of bFGF. The kits may also include an apparatus or container, such as a microplate or dip stick, for conducting the methods of the invention, as well as suitable instructions for carrying out the methods of the invention.

The following examples are presented to demonstrate the methods of the present invention and to assist one of ordinary skill in using the same. The examples are not intended in any way to otherwise limit the scope of the disclosure of the protection granted by Letters Patent granted hereon.

EXAMPLE I

Correlation of bFGF Levels with Breast Cancer bFGF was measured using an ELISA assay (R&D Systems Inc., Minneapolis, Minn.) in the nipple fluid from ten (10) control breasts of human subjects (not identified as having breast cancer, "normals"), four (4) lactating breasts, and ten (10) stage 1 or 2 breasts identified by surgery as having breast cancer.

While the patient was awake, nipple fluid (1–2 drops) was collected with a breast pump which is commonly used by women during lactation. Both normal and cancer patients underwent biopsy. Up to four attempts were typically made in order to elicit nipple fluid. The nipple fluid was stored in a freezer (−20° C.). The data obtained from the analysis of nipple fluid was correlated with the pathologic diagnosis obtained from the surgical specimens.

The ELISA assay was performed as described by the manufacturer for cell supernate, serum and plasma. Briefly, the assay uses *E. coli*-expressed recombinant human bFGF and antibodies raised against the recombinant factor. Anti-bFGF monoclonal antibody is pre-coated onto a microplate. Standards and samples are pipetted into the wells and any bFGF present is bound by the immobilized antibody. After washing away unbound substances, an enzyme-linked anti-bFGF antibody is added to the wells. Following a wash to remove unbound antibody-enzyme reagent, a substrate solution is added to the wells and color develops in proportion to the amount of bFGF bound in the initial step. The color development is stopped and the intensity of the color (optical density of each well) is measured within 30 minutes using a microplate reader set to 450 nm.

Duplicate readings for each standard, control and sample were averaged, and the average zero standard optical density was subtracted. The optical density for the standards versus the concentration of standards was plotted and a best curve drawn. The bFGF concentration of each test sample was determined by locating the absorbance value on the y-axis of the plot and extending a horizontal line to the standard curve. The corresponding bFGF concentration is read off the x-axis. The minimum detectable level of bFGF using this assay is typically less than 3 pg/ml. The results of the assay are shown in (Table 1).

TABLE 1

Nipple Fluid bFGF Concentrations (pg/ml)

| Normal Breasts | Lactating Breasts | Cancer Breasts |
|---|---|---|
| 190 | 1,670 | 7,470 |
| nd*(9) | 1,150 | 2,490 |
|  | 990 | 2,390 |
|  | 450 | 2,240 |
|  |  | 860 |
|  |  | 670 |
|  |  | 590 |
|  |  | 310 |
|  |  | 150 |
|  |  | nd | nd*: not detected

Nipple fluid was obtained from the 24 breasts out of a total attempt on 30 breasts (80% success rate). The detection limit was 100 pg/ml. Control nipple fluids had significantly lower levels of bFGF in comparison to cancer nipple fluids (19±19 pg/ml versus 1,717±706 pg/ml, p=0.027, student's t-test). It is striking that there was very little overlap in the values of bFGF measured in these two groups. The one cancer patient with undetectable levels of bFGF in the nipple fluid already had surgical resection of her cancer at the time of this study. Lactating nipple fluids contained a significant amount of bFGF (1,065±251 pg/ml).

Levels of another potent angiogenic factor VEGF (vascular endothelial growth factor) were also measured in nipple fluids using the same protocol as above for bFGF. There were no significant differences between the three groups: 106,500±19,000 pg/ml in control breasts, 92,400±19,100 pg/ml in cancer breasts, and 46,100±17,800 pg/ml in lactating breasts (p is not significant). These results suggest that VEGF in nipple fluids may not be useful in diagnosing breast cancer.

In addition, the assay was performed on nipple fluid obtained by spontaneous discharge (no pump used).

TABLE 2

Nipple Fluid bFGF Concentrations (pg/ml)

| Normal Breasts | High Risk* Breasts |
|---|---|
| 110 | 1510 |
| 150 | 503 |
| 93 | 1675 |
| 62 | 371 |
| 155 | 525 |
| 93 |  |
| 168 |  |
| nd** (13) |  |

High Risk* = no breast cancer diagnosed, but at high risk as identified by family history or personal history of breast cancer
nd** = not detected These data demonstrate increased levels of bFGF in the nipple fluid from subjects identified as having breast cancer, or at high risk for breast cancer, as compared to levels of bFGF in normal subjects.

EXAMPLE II

Additional Correlation of bFGF Levels with Breast Cancer in Human Subjects

Additional human subjects were tested for bFGF levels, as described above in Example I, supra. 42 patients had benign breast lesions and 20 patients were diagnosed with breast cancer (Table 3)

TABLE 3

Nipple fluid bFGF (pg/ml) and patients' diagnoses

| BFGF Value | Benign Cases | Malignant Cases | Total Cases |
|---|---|---|---|
| <100 | 36 (85.7%) | 1 (5%) | 37 |
| 100–200 | 4 (9.5%) | 4 (20%) | 8 |
| 201–300 | 0 | 1 (5%) | 1 |
| 301–500 | 0 | 3 (15%) | 3 |
| 501–800 | 2 (4.8%) | 4 (20%) | 6 |
| 801–1000 | 0 | 2 (10%) | 2 |
| >1000 | 0 | 5 (25%) | 5 |
| Total | 42 (100%) | 20 (100%) | 62 |

Table 4 shows the results if a level of 100 pg/ml of bFGF is used as a cut-off for detection.

TABLE 4

| bFGF | Benign | Malignant | Total |
| --- | --- | --- | --- |
| Undetected (bFGF < 100) | 36 (85.7%) | 1 (5%) | 37 |
| Detected (bFGF ≧ 100) | 6 (14.3%) | 19 (95%) | 25 |
| Total | 42 (100%) | 20 (100%) | 62 |

(Chi-square test exact p-value < 0.0001)

From these results, the estimated sensitivity of bFGF (the probability of having positive bFGF values for breast cancer patients), is 95% (1/20). The estimated specificity of bFGF (the probability of having negative bFGF values for normal subjects) is 85.7% (36/42). The true positive rate (the probability of having cancer for patients with positive bFGF levels) is 76% (19/25). The true negative rate (the probability of not having cancer for patients with negative bFGF levels) is 97.3% (36/37).

The above Examples demonstrate that measurement of bFGF in nipple fluid has the potential of being a useful diagnostic tool for breast cancer in human subjects.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

What is claimed is:

1. A method for diagnosing breast cancer, or a high risk of breast cancer, in a subject, comprising measuring basic fibroblast growth factor (bFGF) in a test sample of nipple fluid obtained from the subject, and comparing the level of bFGF in the test sample with samples from subjects not having breast cancer, wherein an increase in the level of bFGF in the test sample, as compared to samples from subjects not having breast cancer, indicates breast cancer or the high risk of breast cancer in the subject.

2. The method of claim 1, wherein bFGF in the sample is measured using anti-bFGF antibody.

3. The method of claim 1, wherein the amount of bFGF in the sample of nipple fluid obtained from subjects not having breast cancer is less than 200 pg/ml.

4. The method of claim 1, further comprising the step of detecting at least one additional cancer marker.

5. The method of claim 4, wherein said additional cancer marker is an angiogenic factor.

6. The method of claim 1, further comprising the step of administering a substance to enhance the flow of nipple fluid from the subject.

7. The method of claim 6, wherein the substance is oxytoxin.

8. The method of claim 1, wherein the step of measuring bFGF in the test sample is performed by using a diagnostic kit comprising reagents to measure bFGF in the test sample.

* * * * *